United States Patent [19]

Herold

[11] 4,317,615
[45] Mar. 2, 1982

[54] PROTECTIVE CASE FOR A QUARTZ-ROD OPTICAL WAVE GUIDE

[75] Inventor: Wolf-Dietrich Herold, Hechendorf, Fed. Rep. of Germany

[73] Assignee: ESPE Fabrik Pharmazeurischer Preparate GmbH, Seefeld, Fed. Rep. of Germany

[21] Appl. No.: 56,985

[22] Filed: Jul. 12, 1979

[30] Foreign Application Priority Data

Jul. 18, 1978 [DE] Fed. Rep. of Germany ... 7821507[U]

[51] Int. Cl.³ .......................... G02B 5/14; A61B 1/24
[52] U.S. Cl. ............................... 350/96.32; 350/1.1; 350/96.10; 350/96.20; 350/96.23; 433/126
[58] Field of Search ............. 350/96.10, 96.26, 96.29, 350/96.30, 96.32, 96.34, 1.1, 96.20, 96.23; 433/126, 127, 128

[56] References Cited

U.S. PATENT DOCUMENTS

| 624,392 | 5/1899 | Smith | 350/96.10 X |
|---|---|---|---|
| 1,559,770 | 11/1925 | Paddock | 350/1.1 |
| 1,706,161 | 3/1929 | Hollnagel | 350/96.26 X |
| 1,791,794 | 2/1931 | Chesney | 350/96.26 X |
| 1,838,982 | 12/1931 | Angell | 433/126 |
| 3,101,411 | 8/1963 | Richards | 350/1.1 X |
| 3,370,502 | 2/1968 | Wilks, Jr. | 350/96.10 X |
| 3,641,332 | 2/1972 | Reick et al. | 350/96.32 X |
| 3,752,146 | 8/1973 | Kline | 350/96.10 X |
| 3,901,674 | 8/1975 | Strack et al. | 350/96.30 X |
| 4,009,382 | 2/1977 | Nath | 350/96.26 X |
| 4,129,356 | 12/1978 | Oestreich | 350/96.23 |

FOREIGN PATENT DOCUMENTS

| 2820510 | 11/1978 | Fed. Rep. of Germany | 350/96.23 |
|---|---|---|---|
| 121206 | 7/1927 | Switzerland | 433/126 |
| 1189265 | 4/1970 | United Kingdom | 350/96.32 |

*Primary Examiner*—John K. Corbin
*Assistant Examiner*—John D. Lee
*Attorney, Agent, or Firm*—Bacon & Thomas

[57] ABSTRACT

A quartz rod used as an optical wave guide to direct radiation of a desired spectrum onto a limited area, such as a dental cavity filled with a material curable by the radiation, is protected by a case including at least two rigid shells which tightly enclose the quartz rod but are easy to disassemble for being cleaned, and easy to reassemble thereafter. The interior wall of the case formed by the shells is spaced from the outer surface of the quartz rod except at a few points at both ends of the case, to leave the total reflection characteristics at the quartz rod surface unaffected.

6 Claims, 6 Drawing Figures

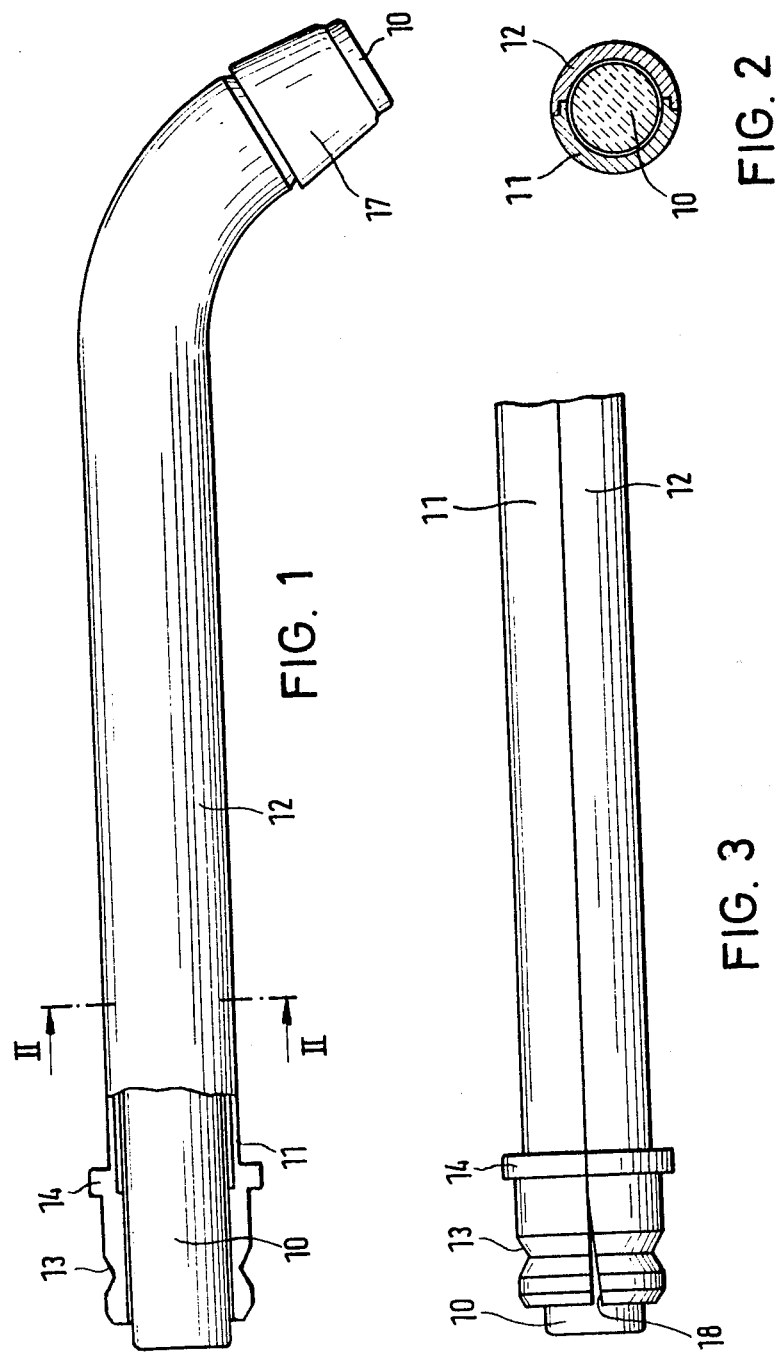

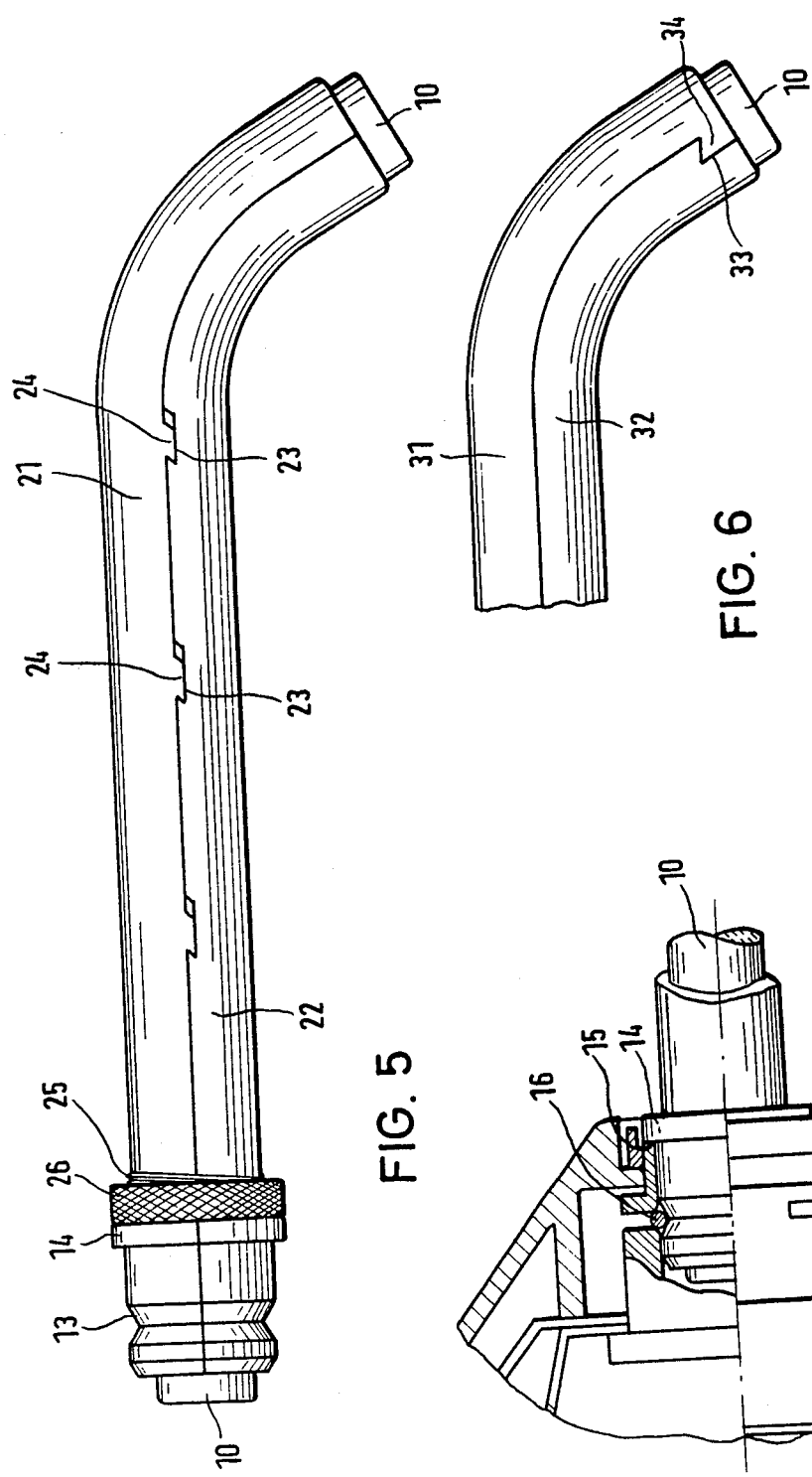

PROTECTIVE CASE FOR A QUARTZ-ROD OPTICAL WAVE GUIDE

BACKGROUND OF THE INVENTION

The present invention relates to a protective case for a quartz-rod optical wave guide in which the interior wall of the case is throughout its major portion spaced from the outer surface of the quartz rod.

If used for polymerizing dental fillings of plastics material, a quartz-rod optical wave guide serves to direct the ultraviolet radiation generated by a light source contained in a hand-held appliance to the location of treatment inside a patient's mouth. Preferably, such quartz rod has a curved light spill end.

It is important to avoid substantial transmission loss of the radiation travelling through the wave guide. A quartz rod acts as an ultraviolet wave guide almost free of loss as long as there is a boundary layer of air surrounding its outer surface. Any surface contact with other materials creates substantial loss, particularly at the curved portion of the wave guide.

For the following two reasons, it is undesirable to use a completely unprotected quartz rod:

(1) A certain amount of radiation escapes to the environment along the outer surface of the quartz rod, especially at curvatures. Such a stray radiation has a blinding effect on the user. Besides, any undesired ultraviolet irradiation is to be generally avoided. According to a regulation set by the American Dental Association, ultraviolet stray radiation in the spectral range from 315 to 400 nm shall be limited to a maximum energy of 1.0 mW/cm$^2$.

(2) A quartz rod is a relatively fragile structural element, so that a protective envelope is desired also for this reason.

German Offenlegungsschrift No. 2,602,956 discloses a protective casing for a quartz-rod optical wave guide, which consists of a tubing shrunk onto the quartz rod, an air boundary layer between the quartz rod and the tubing being created by subsequently slitting the tubing in its longitudinal direction.

A further protective casing for a quartz rod is known from German Offenlegungsschrift No. 2,607,249 in which the curved portion of the quartz rod is surrounded by a helix of metal or plastics which is covered again by a shrink-down tubing. The helix contacts a comparatively small surface area of the uninsulated wave guide.

Another quartz rod available in the market replaces the helix by a plastics netting.

It is important for any parts that are used in patients' mouths that they can be properly cleaned or sterilized. In this connection, the American Dental Association requires any one of the following procedures:

(1) Vapour sterilization for ten minutes in an autoclave at 121° C. and a pressure of 1.075 bar above atmospheric;

(2) dry sterilization at temperatures up to 170° C.;

(3) cleaning by liquid solvents and submerging for 60 minutes in a cold disinfectant solution.

Procedure (3) above is not readily followed in practice as it does not really guarantee a 100-percent sterilization.

The protective cases for quartz-rod optical wave guides of the prior art as mentioned above have serious disadvantages from the cleaning standpoint. Some of the commercially available dry sterilizes employ temperatures of up to 220° C. Unsuited plastics material will be completely destroyed at such temperatures. On the other hand, a synthetic material which would resist these temperatures, such as tetrafluoroethylene, is too expensive.

If wet sterilization is applied, all prior art devices have another serious disadvantage in common. If water enters the space between the quartz rod and the cover, the ability of the quartz rod to guide ultraviolet radiation is drastically reduced (reduction by up to 70 percent). Particularly quartz rods fixedly surrounded by a shrink-down tubing with spacers such as netting or helices disposed between the rod and the tubing are very much exposed to this danger because, even with an intact tubing, the aqueous solution in which the rod is submerged will soon penetrate underneath the tubing along capillaries formed between the spacers. This liquid will not easily drain off subsequently to the cleaning procedure, but will attack metal parts and affect or destroy the function of the entire appliance. If the case consists of a slit tubing, the liquid will drain off, but remainders of the solvent will stay and dry in on the quartz rod surface, thereby progressively impeding the transmission. A sterilization in an autoclave using pressurized vapour of 120° C. will similarly affect the function of the device.

In summary, the protective cases for quartz rods heretofore known are suitable only for being superficially wiped off with a cleaner in order not to jeopardize its proper function, because an absolutely fluid-tight closure at both ends of a shrink-down tubing is never guaranteed.

A further serious disadvantage of a shielding using a fixedly surrounding shrink-down tubing resides in that a fracture in the quartz rod is not easily recognized, since even a completely broken rod will be fixedly supported by the solid tubing.

SUMMARY OF THE INVENTION

It is an object of the invention to avoid the above-mentioned difficulties and disadvantages.

More specifically, it is an object of the invention to provide a protective case for a quartz-rod optical wave guide in which the spacing essential for the guiding of radiation through the quartz rod is insured and which, at the same time, permits easy and complete cleaning and sterilization in accordance with any desired procedure.

To meet with this object, the case of the present invention comprises rigid shells which contact the quartz rod at a minimum of points and which are simply disassembled to ensure complete drying upon sterilization.

In a preferred embodiment of the invention, the shells have stepped edges overlapping each other thereby avoiding any radiation from escaping through gaps that may be caused by manufacturing tolerances at the separation lines of the shells.

In a further preferred embodiment, a sleeve adapted to be slid onto an end portion of the shells serves to hold the shells tightly together and simultaneously prevents the quartz rod from dangling within the case. At the other end, the shells are preferably held together by forming one common circumferential groove adapted to be inserted in, and held by, a socket of the appliance with which the wave guide is used. This embodiment may turn out particularly useful in practice. In another preferred embodiment, the shells are held together at the said other end by a retaining nut screwed onto a common thread formed by the two shells.

In a further advantageous embodiment, at least one of the shells is bevelled at an end portion thereof, whereby the protective case is particularly easily dismantled.

In as much as the quartz rod is inserted into a patient's mouth, the sleeve used for holding the forward ends of the shells together is preferably made of soft plastics material. A particularly light-weight casing is achieved by making the shells of an aluminum alloy.

If the quartz rod is curved, the case is preferably made up of two shells having edges abutting each other in the plane in which the quartz rod is curved, thereby achieving a particularly high stiffness of the shells, thus avoiding gaping of the shells even in their middle portion. Alternatively, the shell edges may be provided with slide latches which hold the shells tightly together in the assembled condition, yet permit easy disassembling thereof.

BRIEF DESCRIPTION OF THE DRAWINGS

FIG. 1 shows a protective case, partly broken away to show the inserted quartz rod, according to a first embodiment of the invention;

FIG. 2 shows a cross section along the line II—II of FIG. 1;

FIG. 3 illustrates the rear portion of the case of FIG. 1, rotated by 90°;

FIG. 4 shows the rear portion of the protective case of FIGS. 1 to 3 inserted into the front end of a hand-held appliance containing an ultraviolet radiation source;

FIG. 5 is a side view similar to FIG. 1 of a protective case according to a second embodiment of the invention, with a quartz rod inserted; and FIG. 6 shows the front end of a protective case according to a modification of the embodiment depicted in FIG. 5.

DETAILED DESCRIPTION OF PREFERRED EMBODIMENTS

The protective case shown in FIGS. 1 to 3 for a quartz-rod optical wave guide 10 which is curved near its front light spill end as also shown in the Figures, consists of two shells 11 and 12 made of an aluminum alloy and abutting each other along separation lines extending in the plane in which the quartz rod is curved. At its edges forming the separation lines, the shell 11 is formed with an inner projecting step, and the shell 12 is formed with an outer projecting step. These steps overlap each other in the assembled condition as shown in FIG. 2, which not only prevents radiation from escaping at the escaping at the separation lines but also—in combination with the curvature—results in a mutual locking of the shells in the axial direction.

At their rear ends, the two generally semicylindrical shells 11 and 12 together form one common annular groove 13 and one common annular flange 14. When the wave guide 10 covered by the shells 11 and 12 is inserted into the front end of the appliance partly shown in FIG. 4, the annular flange 14 engages a front abutting surface 15, and the annular groove 13 engages a resilient ring 16 or a plurality of spring-biassed detent balls provided in the thus designed socket of the appliance for locking the quartz rod. By being inserted into this socket, the shells 11 and 12 are simultaneously held together at their rear end.

A sleeve 17 of soft plastics material is slid onto the front end of the quartz rod and shells to serve the following purposes:

(1) The shells 11 and 12 are mutually fixed. Gaping of shells at their front ends is thereby prevented.

(2) For reasons of manufacture, the diameter of the quartz rod 10 must have a greater negative tolerance than the shells 11, 12. The sleeve 17 removes the free play of the quartz rod.

(3) Should the dentist inadvertently touch a tooth, the contact occurs with the soft plastics of the sleeve 17 rather than with the metal of the shells 11, 12.

(4) The sleeve 17, prevents saliva from entering between the protective case and the quartz rod during the dental treatment.

The sleeve 17 may be made either of heat resistant material such as tetrafluoroethylene, in which case it forms a part to be sterilized; alternatively, it may be molded of a low-cost plastics such as polyethylene, and disposable.

The following manipulations are necessary for disassembling the protective case of FIGS. 1 to 3:

Upon withdrawing the quartz rod from the socket shown in FIG. 4, the sleeve 17 is slid off. Subsequently, the rear ends of the two shells 11 and 12 are compressed between the thumb and forefinger of one hand. Bevelled portions 18 provided in this area at the edges of the shell 12 and extending under an angle of e.g. 4° cause the two shells to open at their forward ends so that the quartz rod 10 may now be grasped with the other hand and withdrawn. In the thus dismantled condition, the quartz rod 10, the two shells 11 and 12, and the sleeve 17 (if re-used) may be cleaned or sterilized in accordance with any desired procedure and dried prior to being reassembled, so that no humidity or foreign material may remain in the critical space between the outer surface of the quartz rod 10 and the interior wall of the protective case. The dismounting provides for the further advantage that any damage of the quartz rod becomes easy to detect. Reassembling the parts is unproblematic as the quartz rod 10 upon being inserted into one of the two shells will serve as a guide for the other shell.

In the embodiment shown in FIG. 5, the protective case consists of two shells 21 and 22 abutting along separation lines lying in a plane which contains the center line of the quartz rod and extends vertically to the plane of curvature of the quartz rod. Just as the shells 11 and 12 in FIGS. 1 to 3, the shells 21 and 22 have stepped edges overlapping each other in the assembled condition. Mutual locking of the shells 21 and 22 is achieved by three parallelogram-shaped recesses 23 provided at both edges of the lower shell 22 which engage corresponding parallelogram-shaped projections 24 formed at the edges of the upper shell 21. The projections 24 are somewhat shorter in the axial direction than the recesses 23 to allow relative movement between the shells 21 and 22 in the axial direction. In the fully assembled condition of the two shells, the left-hand edges of the recesses 23 as viewed in FIG. 5 engage the left-hand edges of the projections 24 in an interlocking manner to prevent gaping of the shells along the separation lines.

At their rear ends the shells 21 and 22 are shaped so as to form together one common thread 25 to be engaged by a retaining nut 26 which may be screwed onto the thread 25 against the annular flange 14 formed by the two shells to hold the shells together. As above, the two shells furthermore form one common annular groove 13 for snap-engagement with the socket of an appliance shown in FIG. 4.

In the modification shown in FIG. 6, Z-shaped recesses 33 are provided at the front end of the lower shell 32 and complementary shaped projections 34 are provided at the front end of the upper shell 31 in addition to, or instead of, the recesses 23 and projections 24 illustrated in FIG. 5. The recesses 33 and projections 34 engage each other in a hingelike manner and again prevent the shells from gaping.

The sleeve 17 of the embodiment shown in FIG. 1 may be used also in combination with the embodiments of FIGS. 5 and 6. Similarly, it is possible to use the retaining nut 26 shown in FIG. 5 also with the embodiment of FIGS. 1 to 3.

The annular groove 13 provided at the rear end of the two shells and cooperating with the socket shown in FIG. 4 provides the following advantages:

(1) Removing and reinserting the quartz rod takes place by simple pull and push motions.

(2) The quartz rod may be rotated 360° about its axis. The retaining force created by the resilient ring 16 (or the resiliently biassed detent balls, respectively) is absolutely uniform.

(3) The resiliency absorbs tolerances of the fitting as it acts on the conical annular groove 13, thereby pulling the protective case with its annular flange to abut against the socket. The quartz rod is thus retained without free play.

(4) When inserting the quartz rod, the cylindrical socket of the appliance renders the retaining nut 26 unnecessary if the case is divided into shells as shown in FIGS. 1 to 3, or if, as in the embodiments of FIGS. 5 and 6, locating pins are provided at the rear ends of the shell edges, which makes the case even simpler to assemble and disassemble.

The advantages achieved with the above described protective case for a quartz-rod optical wave guide are summarized below:

(1) With the rigid shells forming a protective case the inner diameter of which is only slightly greater than the outer diameter of the quartz rod, contact is made only at three to four points, while an air boundary layer is maintained at all other locations. This ensures optimum transmission of radiation along the quartz rod.

(2) The mutually overlapping shells, which preferably consist of metal or a suitable rigid plastics material, reliably guarantee complete radiation tightness.

(3) The protective case simultaneously provides for reliable mechanical protection of the quartz rod.

(4) The protective case is easy to disassemble and thus convenient and thorough to clean or sterilize in accordance with any desired procedure.

(5) Fractures in the quartz rod are immediately detected in the dismounted condition.

(6) The snap-in connection between the quartz rod and the socket of the appliance allows quick replacement and rotation of the quartz rod with respect to the socket, which is of particular advantage if the device is used by a dentist for treating dental fillings.

I claim:
1. A quartz-rod optical waveguide comprising:
   an elongated quartz rod;
   a casing surrounding and enclosing said quartz rod, said casing comprising at least two separate rigid shells having edges tightly abutting each other along separation lines extending parallel to the center line of the quartz rod;
   the major area of the inner surface of the casing being spaced from the outer surface of the quartz rod;
   said shells having stepped edge portions overlapping each other;
   the edges of one shell diverging from those of another shell at adjacent end portions of the shells.

2. The waveguide of claim 1, wherein the shells have end portions shaped to form together one common circumferential flange adapted for engaging a socket of an appliance.

3. The waveguide of claim 2, wherein the shells have end portions shaped to form together a thread adapted to engage a retaining nut which may be tightened against said flange.

4. A quartz-rod optical waveguide comprising:
   an elongated curved quartz-rod;
   a casing surrounding and enclosing said quartz rod, said casing comprising two separate rigid shells having edges tightly abutting each other along separation lines lying in a surface containing the center line of the quartz rod;
   the major area of the inner surface of the casing being spaced from the outer surface of the quartz rod;
   said shells having stepped edge portions overlapping each other;
   means for detachably connecting adjacent first end portions of the shells;
   the adjacent second end portions of said shells being shaped to form together one common circumferential groove adapted for snap-in engagement with a socket of an appliance.

5. The waveguide of claim 4, wherein said means for connecting said shells includes a sleeve slidably embracing said first end portions of the shells, with an outer end portion of the sleeve contacting the quartz rod.

6. The waveguide of claim 4, wherein said means for connecting said shells comprises Z-shaped recesses and projections formed at said first end portions of the shells for mutual engagement in a hinge-like manner.

* * * * *